(12) United States Patent
Yamashita

(10) Patent No.: US 8,056,563 B2
(45) Date of Patent: Nov. 15, 2011

(54) NIPPLE PROTECTOR AND METHOD

(75) Inventor: Daisuke Yamashita, Tokyo (JP)

(73) Assignee: Pigeon Corporation, Tokyo (JP)

( * ) Notice: Subject to any disclaimer, the term of this patent is extended or adjusted under 35 U.S.C. 154(b) by 256 days.

(21) Appl. No.: 12/484,432

(22) Filed: Jun. 15, 2009

(65) Prior Publication Data

US 2009/0308405 A1 Dec. 17, 2009

(30) Foreign Application Priority Data

Jun. 13, 2008 (JP) .................. 2008-155727

(51) Int. Cl.
 A61J 13/00 (2006.01)
 A61M 1/06 (2006.01)
 A61B 18/18 (2006.01)
 A61B 5/00 (2006.01)
(52) U.S. Cl. ............. 128/890; 604/74; 606/13; 600/573
(58) Field of Classification Search .................. 128/846, 128/889, 890; 450/1, 37; 604/347, 346, 604/327, 317
See application file for complete search history.

(56) References Cited

U.S. PATENT DOCUMENTS

| 3,840,012 | A | | 10/1974 | Rushton, Jr. | |
|---|---|---|---|---|---|
| 4,270,538 | A | * | 6/1981 | Murphy | ................. 604/346 |
| 5,100,406 | A | | 3/1992 | Panchula | |
| 2003/0073930 | A1 | | 4/2003 | Morrissey et al. | |
| 2006/0157065 | A1 | * | 7/2006 | Rohrig | .................... 128/890 |

FOREIGN PATENT DOCUMENTS

| EP | 0 442 758 A1 | | 8/1991 |
|---|---|---|---|
| EP | 1 197 198 A1 | | 4/2002 |
| GB | 2 357 434 A | | 6/2001 |
| GB | 2357434 A | * | 6/2001 |
| WO | 96/26703 A1 | | 9/1996 |

OTHER PUBLICATIONS

European Search Report for EP09 25 1533 dated Oct. 1, 2009.
EP Office Action for EP Application No. 09 251 533.7-2124 dated Nov. 12, 2010.

* cited by examiner

*Primary Examiner* — Patricia Bianco
*Assistant Examiner* — Tarla Patel
(74) *Attorney, Agent, or Firm* — Kenealy Vaidya LLP

(57) ABSTRACT

A nipple protector is provided, which is able to protect a nipple of a user reliably, by protecting the nipple area so as to maintain a non-contact state with the nipple area and thereby avoiding the causing of pain or unpleasant irritation to the nipple area, as well as avoiding the leaving of marks while reducing irritation when abutted against the breast. A nipple protector having a hard outer member or shell and an inner member made of a material which is more flexible and deformable than the outer member, with an internal space being formed inside the nipple protector, wherein the internal space is formed by a cylindrical portion which extends from the outer member and/or the inner member, and the inner member has an abutting section which surrounds with no gap the nipple area of a wearer completely, and the abutting section is a deformable abutting section which deforms elastically and is capable of making contact, with no gap, with the perimeter of the nipple area.

16 Claims, 8 Drawing Sheets

NIPPLE PROTECTOR AND METHOD

This application claims the priority benefit under 35 U.S.C. §119 of Japanese Patent Application No. JP2008-155727 filed on Jun. 13, 2008, which is hereby incorporated in its entirety by reference.

BACKGROUND

1. Field

The presently disclosed subject matter relates to a nipple protector and method for covering and protecting a nipple area, and more particularly a woman's nipple area.

2. Description of Related Art

Mothers in the lactation period, for example, suffer damage or soreness of the nipple area due to biting by the infant during nursing, and the like.

If there are problems of this kind in the nipple area, then the flow of breast milk during nursing can be impaired by stress caused by pain. As a consequence, the infant sucks repeatedly with greater force in an attempt to extract a greater amount of breast milk, the nursing time becomes longer, and therefore the damage to the nipple area can become even worse.

Therefore, nipple protectors are used in order to cover and protect the nipple area when the woman is not nursing.

As a nipple protector used in this kind of application, there is, for example, the composition shown in FIG. 8 (see Japanese Patent Application Publication No. 5-33202).

In FIG. 8, the nipple protector 1 includes a hemispherical or dome-shaped shell 2, and an elastic member 3 which serves to close off the base portion of this shell 2. An opening 6 is formed centrally in the elastic member 3. A plurality of air holes (not illustrated) are formed in the shell 2.

As shown in FIG. 9, the nipple protector 1 of this kind prevents any contact with the damaged nipple area 5 and prevents unwanted external irritation of the nipple area 5, by means of the elastic member 3 abutting against the front face of the breast 4 of the user, the nipple area 5 being introduced through the opening 6 in the elastic member 3 and the nipple area 5 then being accommodated in an internal space S1 which is demarcated by the elastic member 3 and the shell 2.

However, a nipple protector 1 of this kind involves certain characteristics, features, and problems such as the following.

The nipple protector 1 protects the nipple area 5 by accommodating the damaged nipple area 5 inside a relatively hard shell 2.

However, there is a drawback in that, when the nipple protector 1 is worn, the hard shell 2 presses against the front face of the user's breast 4 and if the hard outer edge is pressed strongly, then a circular red mark may be left on the front face of the breast 4 and the user may feel pain in the place where the edge digs into the breast.

Therefore, by disposing an elastic member 3 in a position which abuts against the front face of the breast 4 and causing this elastic member to deform in a flexible fashion, pressing of the breast 4 and unpleasant irritation of the breast 4 can be eliminated.

However, as shown in FIG. 8, if the nipple protector 1 is pressed against the front face of the user's breast 4 while being worn, the elastic member 3 deforms and bends toward the inner side. Therefore, the internal space S1 formed by the shell 2 and the elastic member 3 is squashed and becomes smaller, and the inner face of the shell 2, for example, abuts directly against the nipple area 5 accommodated therein, thus causing pain and unpleasant irritation due to rubbing.

In other words, a conventional nipple protector 1 may not be able to provide the function of protecting the nipple area 5 so that it does not come into contact with other objects.

SUMMARY

The presently disclosed subject matter was devised in response to and in an attempt to resolve problems such as those described above, an aspect thereof being to provide a nipple protector which is able to protect the nipple area of a user reliably, by protecting the nipple area so as to maintain absence of contact with the nipple area and thereby avoiding the causing of pain or unpleasant irritation to the nipple area, as well as possibly avoiding the leaving of marks by reducing irritation when abutted against the breast.

According to a first aspect of the presently disclosed subject matter, a nipple protector can include an outer member in a hard shell shape which forms the outer surface of the nipple protector and an inner member made of a material which is more flexible and deformable than the outer member, with an internal space being formed inside the nipple protector, wherein the internal space can be formed by a cylindrical portion which extends from the outer member and/or the inner member; and the inner member has a deformable abutting section which deforms elastically and is capable of making close contact, with no gap, with the perimeter of the nipple area of a wearer.

According to another aspect of the presently disclosed subject matter, since the outer member is formed from a hard material, then it is able to cover the internal space and reliably protect the nipple area (of the wearer) which is accommodated in the internal space, from external forces.

In particular, since the nipple area of the wearer, which is the object of protection, can be accommodated inside the internal space formed by a cylindrical portion extending from the outer member and/or the inner member, then the nipple area can be protected in a non-contact fashion without any portion of the outer member pressing against the nipple area, and consequently, pain or unpleasant irritation to the user's nipple area can be prevented.

Moreover, the deformable abutting section which abuts against the front face of the user's breast can deform upon contact and can make close and uninterrupted contact about the perimeter or the nipple area, thus making it possible to prevent leaking of breast milk. Furthermore, since the deformable abutting section is able to make close face-to-face contact (with the front face of the breast), then compared with a case where the contact is in a line shape, or the like, the contact surface area can be larger, the stimulation caused by is the contact can be reduced and the sealing function can be performed more reliably.

According to another aspect of the presently disclosed subject matter, the internal space can be formed by a cylindrical portion which extends from the inner member.

According to another aspect of the presently disclosed subject matter, since the cylindrical portion can surround and protect the user's nipple area, then it is possible to maintain a non-contact state without any portion of the outer member pressing against the nipple area.

According to another aspect of the presently disclosed subject matter, the cylindrical portion can be a surrounding section which surrounds the nipple area, and the front end of the surrounding section can be formed so as to abut against the inner side of the outer member.

According to another aspect of the presently disclosed subject matter, since the surrounding section can be supported by an outer member against which the surrounding section formed by the cylindrical portion abuts, then it is possible to protect the user's nipple area in a suitable fashion, while maintaining a substantially constant volume of the internal space formed by the cylindrical portion. Furthermore, since the deformable abutting section can be pressed appropriately against the front face of the user's breast, then it is possible to achieve elastic contact in a reliable fashion.

According to another aspect of the presently disclosed subject matter, the internal space can be formed by cylindrical portions which extend respectively from the outer member and the inner member, the cylindrical portion extending from the outer member can form a hard supporting section which surrounds the perimeter of the nipple area of the wearer, and the surrounding section which is the cylindrical portion extending from the inner member can form an installation section which covers the front end portion of the supporting section and also can surround, with no gap, the nipple area completely.

According to another aspect of the presently disclosed subject matter, since the hard supporting section which can be the cylindrical portion extending from the outer member surrounds the perimeter of the nipple area and does not deform, then it is possible to prevent even more effectively a situation where a portion of the outer member is pressed against the nipple area, and since the surrounding portion of the flexible inner member can be installed on the front end portion of the hard supporting section and covers same, then the sealing properties can be improved.

According to another aspect of the presently disclosed subject matter, the surrounding section of the inner member can have a wall section allowing no gap (i.e., a gapless wall section), and as a continuation from the wall section, a bend section which curves inwards on an inner side thereof can be provided, and as continuations from the bend section, the deformable abutting section which expands outwards, and an abutting and protecting section which bends outwards on the outer side of the deformable abutting section and covers the outer edge of the outer member can be provided.

According to another aspect of the presently disclosed subject matter, the surrounding section of the inner member can have a wall section and, formed integrally with same, a bend section which bends inwards. Therefore it can be possible to make the deformable abutting section deform appropriately and abut against the front face of the user's breast by means of the bending and deforming function of the bending section. Moreover, since there can be an abutting and protecting section which bends outwards on the outside of the deformable abutting section and covers the outer edge of the outer member, then it is possible to achieve suitable protection without the outer edge section digging into the front face of the breast.

According to another aspect of the presently disclosed subject matter, an opening which connects the interior space surrounded by the surrounding section to the exterior can be provided in the inner member, and a through-hole which connects to the opening can be provided in the outer member.

According to another aspect of the presently disclosed subject matter, even if breast milk is secreted from the nipple area accommodated in the internal space, this milk can pass through the opening in the inner member and can exit to the exterior by passing through the through-hole in the outer member. Therefore it is possible to absorb this milk by duly positioning a breast pad, or the like.

According to another aspect of the presently disclosed subject matter, an opening having a larger surface area than the opening or the through-hole can be formed in a position of the inner member on the outside of the opening and/or a position of the outer member on the outside of the through-hole.

According to another aspect of the presently disclosed subject matter, since an opening having a larger surface area than the opening can be provided in a position of the inner member to the outside of the opening and/or a position of the outer member to the outside of the through-hole, then even though two or more members are used in the nipple protector formed by assembling together the inner member and the outer member, the weight can be reduced correspondingly by the large opening thus formed. Therefore the overall weight can be minimized. Consequently, when the nipple protector is in a fitted state, the possibility of positional deviation can be minimized and the fitted state can be maintained satisfactorily.

Furthermore, it is also possible to prevent a stifling sensation caused by close contact of the full surface of the deformable abutting section.

As described above, according to the presently disclosed subject matter, it is possible to provide a nipple protector which is able to protect the nipple area of a user reliably, by protecting the nipple area so as to maintain absence of contact with the nipple area and thereby avoiding the causing of pain or unpleasant irritation to the nipple area, as well as avoiding the leaving of marks by reducing irritation when abutted against the breast.

DESCRIPTION OF EXEMPLARY EMBODIMENTS

Below, examples of embodiments of the presently disclosed subject matter are described in detail with reference to the accompanying drawings.

The embodiments described below are concrete examples of the presently disclosed subject matter and therefore are subject to various desirable technical restrictions, but it should be noted that the scope of the present invention is not limited to these specific examples.

Figure 1:
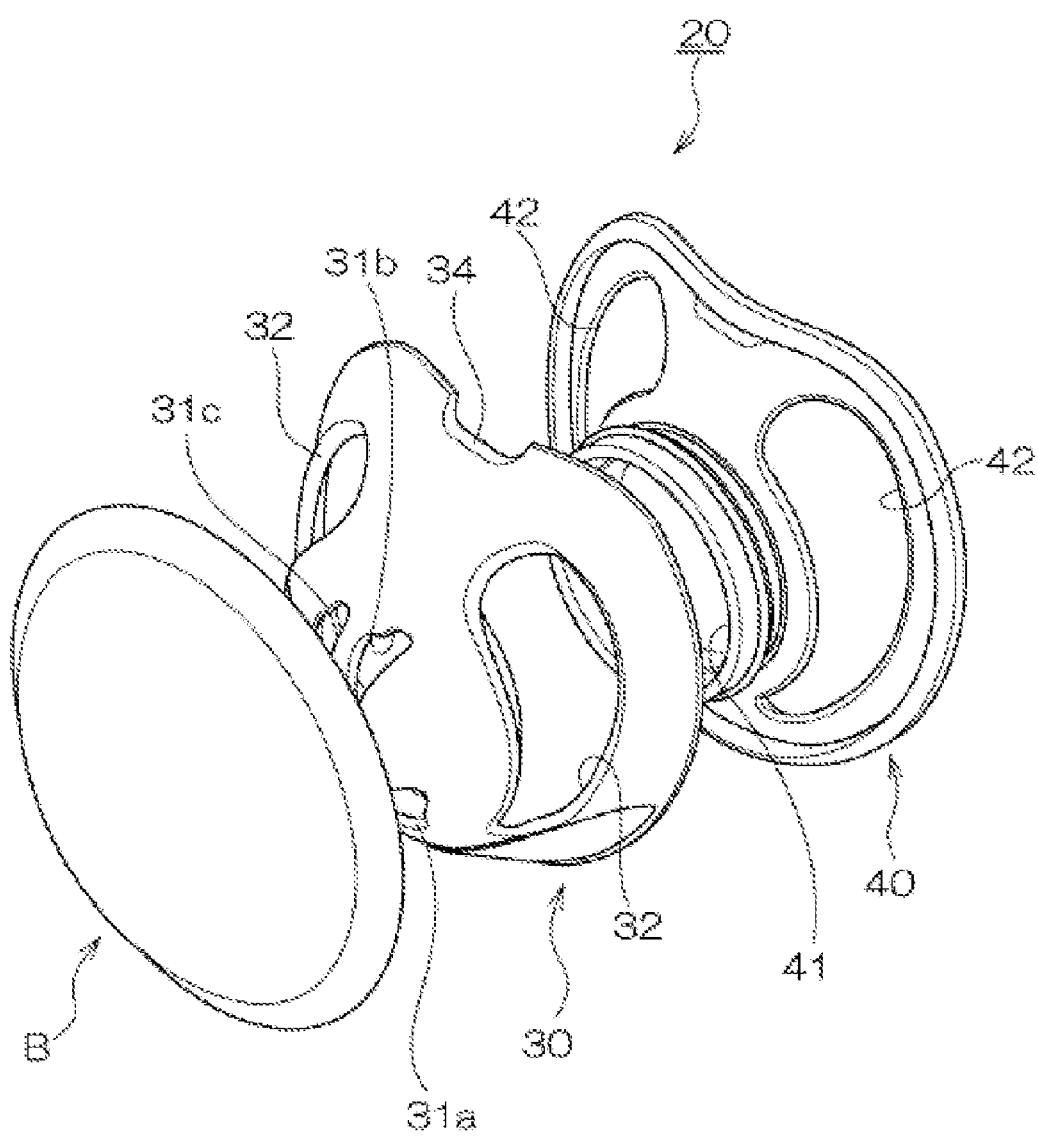
FIG. 1 is an exploded perspective view of a nipple protector according to a first embodiment of the presently disclosed subject matter.
Figure 2:
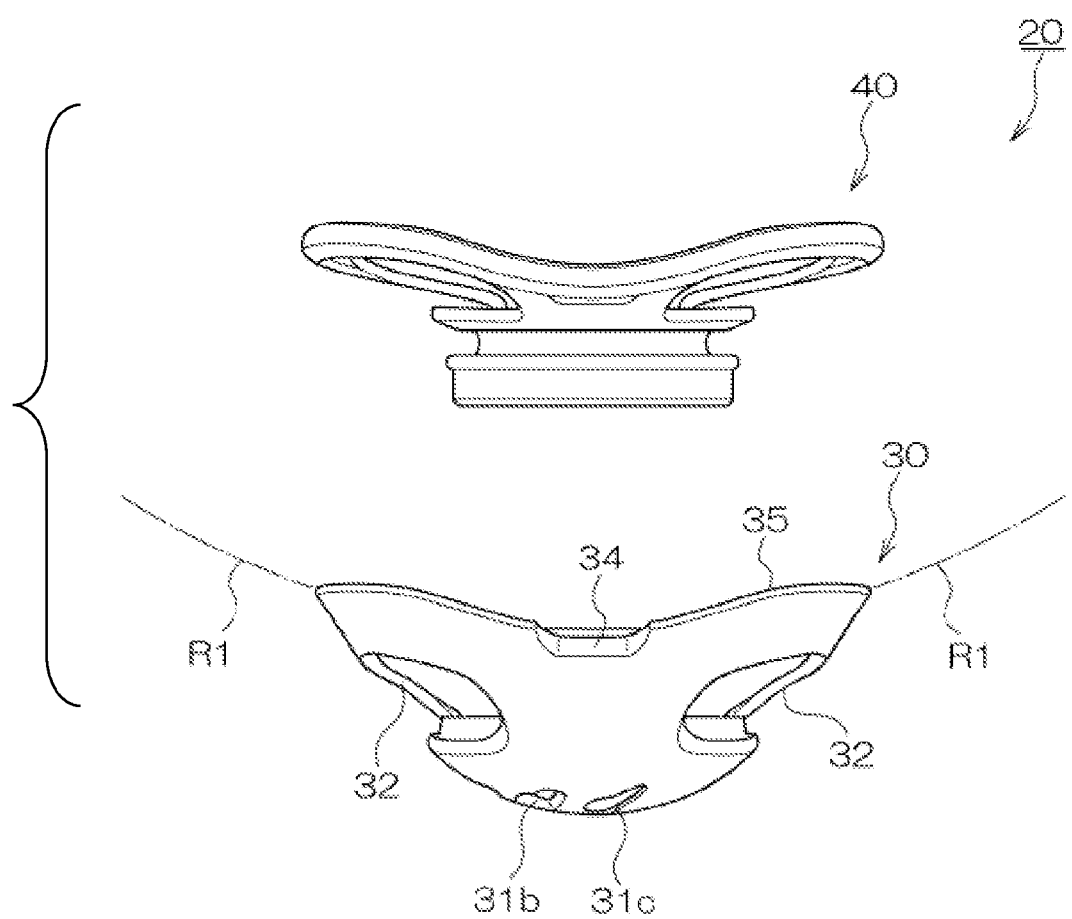
FIG. 2 is an exploded plan view of the nipple protector of FIG. 1.
Figure 3:
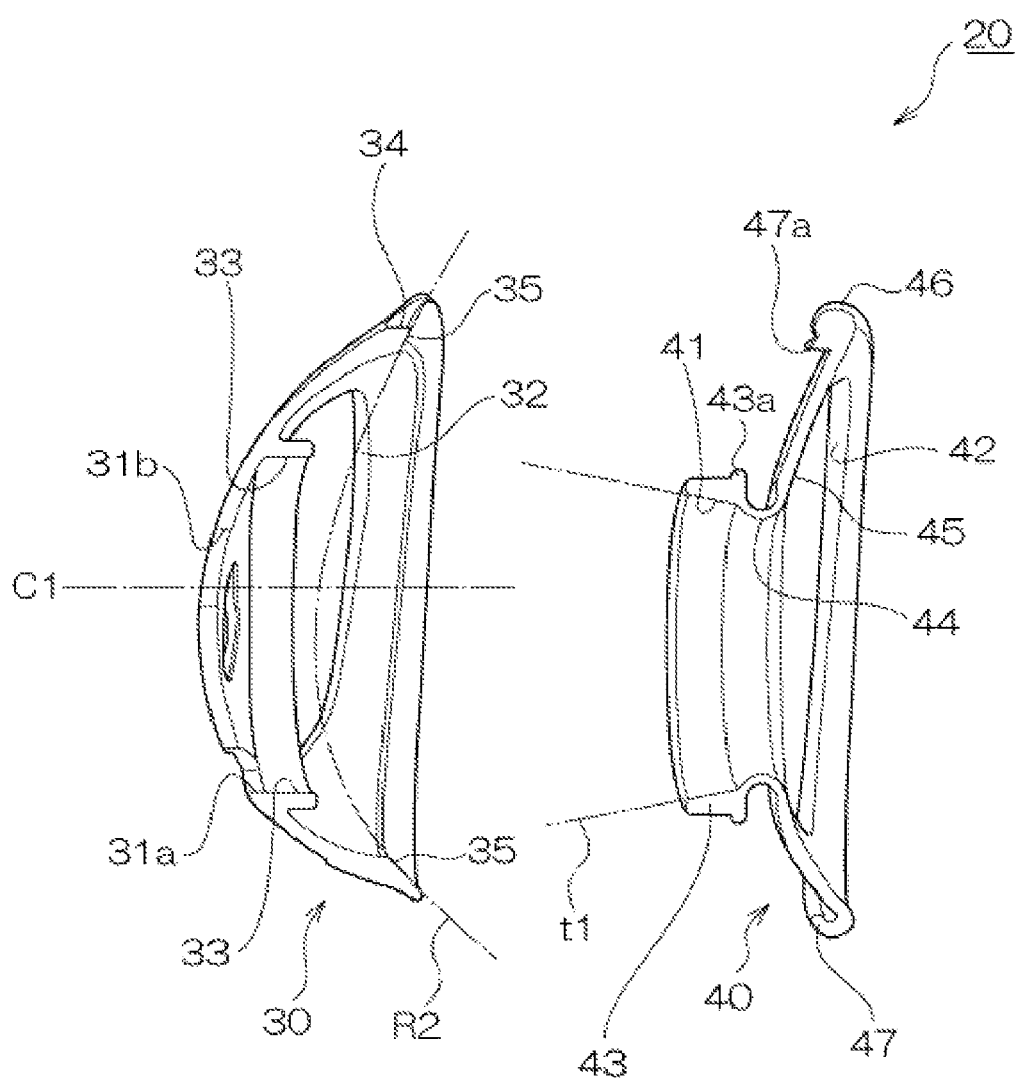
FIG. 3 is an exploded side cross-sectional view of the nipple protector of FIG. 1.
Figure 4:
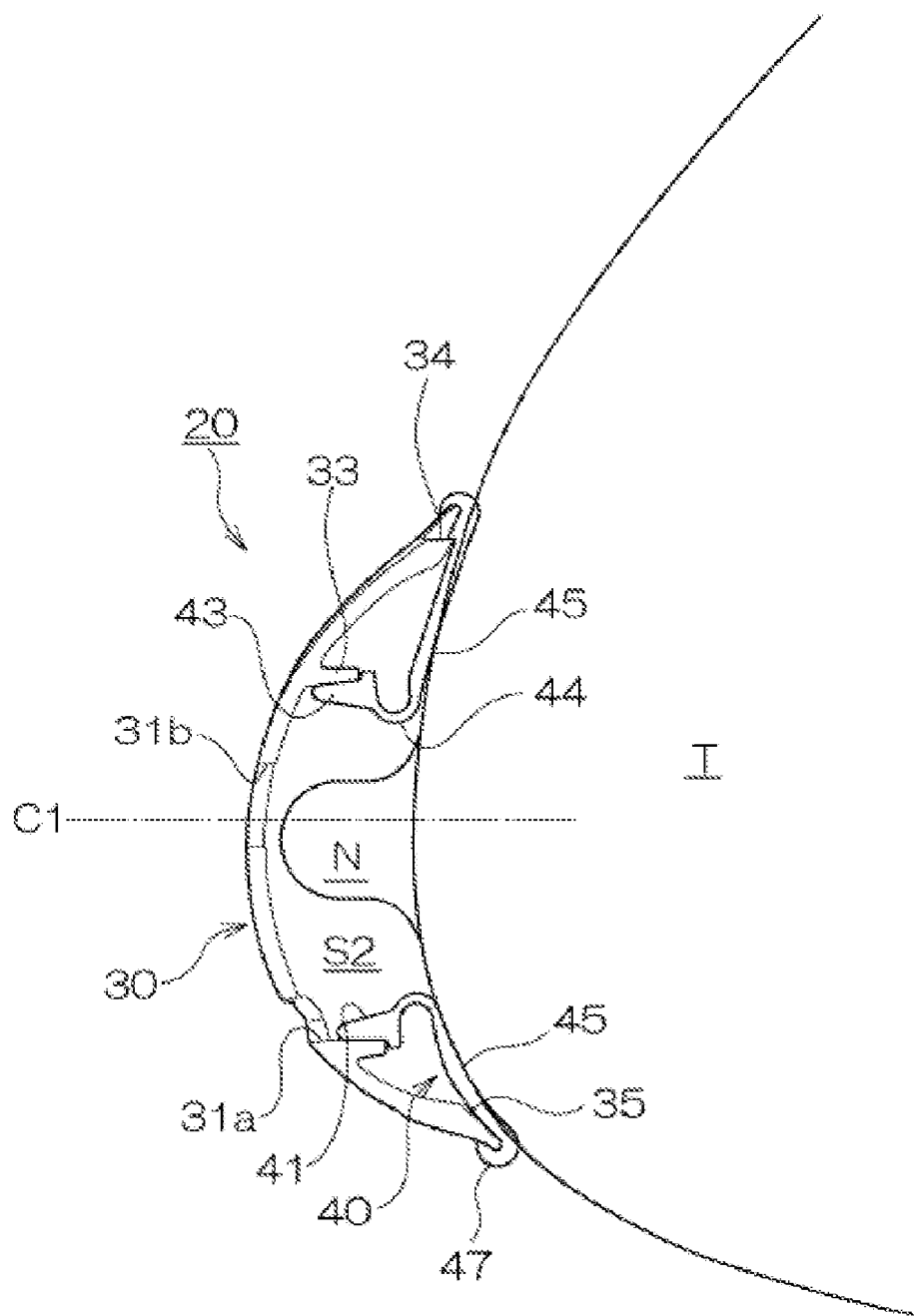
FIG. 4 is a vertical cross-sectional view showing a state where a user is wearing the nipple protector of FIG. 1.

FIG. 1 is an exploded perspective view showing a nipple protector relating to a first embodiment in accordance with the presently disclosed subject matter, FIG. 2 is an exploded plan view of a nipple protector, FIG. 3 is a vertical cross-sectional view showing an exploded view of the nipple protector, FIG. 4 is a vertical cross-sectional view of the nipple protector abutting against the front face of the breast of a user.

An embodiment of a nipple protector is described in detail with reference to these drawings.

The nipple protector 20 can be formed by combining an outer member 30 forming a guard portion which can be a molded member made of hard plastic having overall an approximate shell shape or an approximate dome shape or hemispherical shape, and a flexible inner member 40 that includes a breast abutting portion which can be installed on the inner side of the outer member (in FIG. 1, the "rear side").

As can be seen from FIG. 1, the outer shapes of the outer member 30 and the inner member 40 can have heart shapes which and can be close to a circular shape, when viewed from the front side, for example. Therefore, the outer member 30 and the inner member 40 can adopt a mode which has vertical orientation. In other words, the outer member 30 and the inner member 40 can have a mode where the up/down direction during installation can be readily apparent to the user.

The outer member 30 can be a hard plastic molding made of PP (polypropylene), for example. The material of the outer member 30 is not limited to polypropylene. Any material which is moldable and has an appropriate hardness can be used.

The outer member 30 can be substantially dome-shaped or hemispherical-shaped, and the inner portion thereof can have a concave shape so as to form a space (see internal space S2 in FIG. 4).

Through-holes, which can pass from the interior to the exterior, can be formed approximately in the central portion of the outer member 30. In an exemplary embodiment, a plurality of through-holes can be formed, as indicated by reference numerals 31a, 31b and 31c. Of the plurality of through-holes, one of the through-holes 31a can be disposed below the virtual central line C1 in the vertical direction (or height direction), as shown in FIG. 3 and FIG. 4.

Large openings 32 having shapes with left/right symmetry can be formed respectively in the region outside the central portion of the outer member 30 where the through-holes 31a, 31b and 31c are formed. If at least two of the openings 32 are combined, they can be provided with a larger opening surface area than the total opening surface area of the through-holes 31a, 31b and 31c, and can be formed in a comma-shape. This comma shape can avoid the central portion of the outer member 30, forming a large circular arc in the upper portion and tapering to a narrow end in the lower portion.

The large openings 32 can be formed by removing the material of the outer member 30. In this way, it is possible to reduce the weight of the nipple protector 20. Accordingly, when the nipple protector 20 is installed, it is possible to prevent effectively the occurrence of deviation in the installation position due to reduction in the overall inertia. Furthermore, even when the deformable abutting section lies in close contact with the breast, it is possible to ensure passage of air by means of the openings 32, and therefore it is possible to prevent a stifling sensation caused by the close contact.

Moreover, as shown in FIG. 3, a supporting section 33 can be formed which can have a cylindrical portion that extends inwards (toward the right-hand side in FIG. 3) from the inner side (rear side) of the outer member 30 to at least a position slightly to the outer side of the through-holes 31a, 31b and 31c. The supporting section 33 can be made of a hard material and can be integrally formed as a single homogenous piece with the outer member 30. The supporting section 33 can be a wall-shaped rib which can extend substantially parallel to the virtual central line C1, as shown in FIG. 3.

In this embodiment, the rib forming the supporting section 33 can be configured as an uninterrupted wall so as to surround the region to the outside of the central region where the through-holes 31a, 31b and 31c are formed. With this configuration, it is possible to form a space inside the supporting section 33 that can be maintained at a substantially constant volume since it is demarcated by the hard supporting section 33.

A positioning section 34 that can be configured as a recess, for example, can be formed in the upper end position of the outer member 30. As described below, this recess 34 can guide the outer member 30 to an accurate installation position, when assembled together with the inner member 40.

Furthermore, the perimeter edge section 35 of the outer member 30 can be formed with a planar or curved surface of a shape that substantially follows the curves R1 (see FIG. 2) and R2 (see FIG. 3) of the outer surface of the breast T, taking account of the fact that the nipple protector 20 is disposed on the front face of the breast T of the user, as shown in FIG. 2 and FIG. 4.

The perimeter edge section 35 can be a planar surface or curved surface of narrow width which can substantially follow the curves R1 and R2 of the outer surface of the breast T.

Here, R1 in FIG. 2 is the curved surface produced by the shape of the breast T projecting in the forward direction, when viewed from above, and R2 in FIG. 3 represents the curved surface of same when viewed from the side.

By providing the perimeter edge section 35 of the outer member with a surface area of a prescribed width, it is possible to cause the deformable abutting section to make face to face contact with the breast in conjunction with the function of the deformable abutting section described below, when the outer member 30 abuts the front face of the breast T of the user via the inner member.

Next, the inner member 40 will be described. The nipple protector 20 can prevent external forces of any kind from acting on the nipple area which is accommodated in the internal space and preventing direct contact with external objects, due to the fact that the hard outer member 30 does not deform. In addition, the inner member 40 can prevent the inner surface of the nipple protector 20 itself from touching the injured nipple area. That is, when the nipple protector 20 is installed, the inner member 40 can serve as a shock absorber that can prevent the hard outer member 30 from abutting directly against the user's skin and creating unpleasant irritation.

In order to provide this function, the inner member 40 can be formed entirely from a soft material (e.g., material that is relatively softer than the material from which the outer member is made). For this soft material, it is possible to use silicone, for example. The material for forming the inner member 40 can have a hardness of 50 as measured using a JIS (K6253) type durometer, for example. The hardness of the material can vary with the thickness of the material, and the like. The hardness can be approximately within the range of 35 to 65, with a view to being able to achieve the functions and actions described below in the relation to the presently disclosed subject matter, as well as obtaining shape retaining properties and formability, and the like.

For the material of the inner member 40, it is possible to use a material other than silicone which is more pliant than the outer member 30, which deforms readily by having a certain degree of rubber elasticity, and which has excellent formability.

The outer shape of the inner member 40 can approximate that of the outer member 30, and their respective outer shapes can be virtually superimposed.

In other words, the overall shape of the inner member 40 can be a heart shape which is close to a circular shape, and can include a cylindrical opening 41 in the central portion. The cylindrical opening 41 can be a through-hole. The inner side of the cylindrical opening 41 can form an internal space S2.

Large openings 42 forming shapes with left/right symmetry can be formed respectively in the region to the outside of the central portion where the cylindrical opening 41 is formed. If at least two openings 42 are aligned, they can be provided with a larger opening surface area than the opening surface area of the cylindrical opening 41, and can be formed in a comma-shape which avoids the central portion of the outer member 30, forming a large circular arc in the upper portion and tapering to a narrow end in the lower portion.

The large openings 42 can be formed by removing the material in the inner member 40. In this way, it is possible to reduce the weight. Accordingly, when the nipple protector 20 is installed, it is possible to prevent effectively the occurrence of deviation in the installation position due to reduction in the overall inertia. Furthermore, even when the deformable abutting section lies in close contact with the breast, it is possible to ensure passage of air by the openings 32 and therefore it is possible to prevent a stifling sensation caused by the close contact.

In FIG. 3 and FIG. 4, in the inner member 40, the perimeter edge of the cylindrical opening 41 can form a low cylindrical portion which can extend from the perimeter edge of the opening. This cylindrical portion can form a surrounding section which surrounds the perimeter of the nipple area N of the user. Moreover, in this exemplary embodiment, the surrounding section can form an installation section 43 for installing the supporting section 33 of the outer member 30 on the inner member 40.

The installation section 43 can be provided with an interlocking step section 43*a* which can be configured as a laterally-oriented step section. The step section 43*a* can be fitted into the supporting section 33 formed by the wall-shaped rib of the outer member 30. The step section 43 can be formed on the outside of the installation section 43 so that the step section 43*a* can abut against the front end of the supporting section 33 when fitted into the supporting section 33.

In other words, when installed, the installation section 43 can cover the front end of the supporting section 33. Furthermore, the cylindrical opening 41 on the inner side of the installation section 43 can be tapered so as to open toward the front direction, as indicated by the broken line t1 in FIG. 3.

A bend section 44 can be connected to the installation section 43 of the inner member 40. A deformable abutting section 45, which can extend toward the outer circumferential direction, can be connected to this bend section 44.

The inside portion of the bend section 44 that forms a base end portion of the installation section 43 can have a shape which bends to the inside, and the final end portion of the bend section 44 can include a curved surface which is substantially the same as the curves R1 and R2 in FIG. 2 and FIG. 3. In other words, the final end portion can have a curved surface which is slightly convex in the downward direction, as viewed in FIG. 2, and in the leftward direction, as viewed in FIG. 3, and which becomes the deformable abutting section 45 described above.

Moreover, the outer edge portion of the deformable abutting section 45 can be curved outwards and can form an abutting and protecting section 46 which covers the outer edge of the outer member 30.

As can be seen from FIG. 3, the outer edge portion of the inner member 40 can form an attachment section 47 which can have a groove that is open obliquely in the forward direction. The attachment section 47 can enable the inner member 40 to be readily attached to and detached from the outer member 30 via the outer edge portion of the outer member 30. Specifically, the outer edge portion of the outer member 30 can be fitted into and detached from the groove in the attachment section 47.

Moreover, an engaging section 47*a* can be formed as an engaging hook projecting in the forward direction, for example. The engaging portion 47*a* can be formed on the upper end position of the inner member 40. By inserting this engaging section 47*a* into the positioning section 34 of the outer member 30, it is possible to correctly position and combine the outer member 30 and the inner member 40.

The present embodiment described above can be used as follows.

Figure 5:
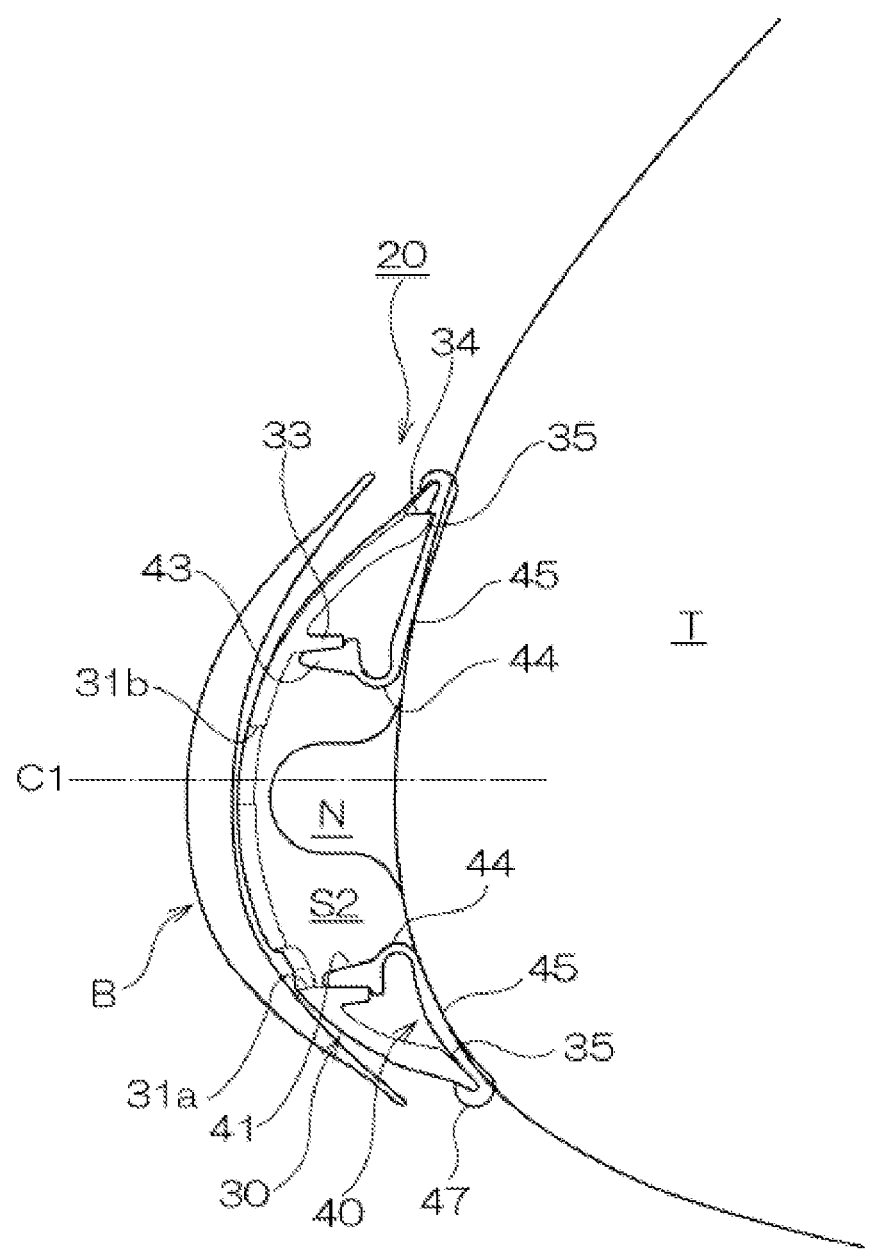
FIG. 5 is a vertical cross-sectional view showing the nipple protector of FIG. 1 in a use state.

FIG. 5 shows a state where the nipple protector 20 is disposed on the front face of the breast T of a user. A breast pad B can be placed against the outer side thereof, and can be held in place by underwear, such as a bra (not illustrated).

In the nipple protector 20 according to the presently disclosed subject matter, since the outer member 30 can be formed from a hard material, then it is able to cover the internal space S2 and reliably protect the nipple area N (of the wearer) accommodated in the internal space S2 from external forces.

Here, in cases where the nipple area N accommodated in the internal space S2 is injured, then if the internal space S2 is crushed and constricted, due to the elastic deformation of the outer surface of the nipple protector 20, for instance, then the inner side (inner surface) of the nipple protector 20 can make contact with the nipple area N, thus causing unpleasant irritation, pain, and the like.

However, in the present embodiment, since the outer member 30 can include a hard wall-shaped supporting section 33 which can surround the perimeter of the nipple area N, then deformation of the internal space S2 can be prevented and the nipple area N can be protected by means of the hard supporting section 33 which surrounds the perimeter thereof. Consequently, since the nipple area N can be protected in a non-contact fashion without being pressed by any portion of the outer member 30, then pain or unpleasant irritation to the user's nipple area N can be prevented.

Instead of the hard supporting section 33 of the outer member 30, it is also possible to form an internal space S2 by a cylindrical portion extending from the inner member 40. In this alternate exemplary arrangement, the nipple area N can also be protected.

Furthermore, since the installation section 43 of the flexible inner member 40 can be formed so as to cover the front end portion of the hard supporting section 33, then contact by the hard supporting section 33 with the user's breast T can be avoided, thereby preventing unpleasant irritation or pain.

Moreover, the deformable abutting section 45 can make close and continuous face-to-face contact with the perimeter of the nipple area N. In other words, in the inner member 40, the deformable abutting section 45 which abuts against the front face of the user's breast T can deform upon contact with the user's breast T and can make close and uninterrupted contact about the perimeter of the nipple area N, thereby making it possible to prevent breast milk from leaking to the exterior from the internal space S2. Moreover, since the deformable abutting section 45 is able to make close face-to-face contact (with the front face of the breast T), then compared with a case where the contact is in a line shape, or the like, the contact surface area is larger, the stimulation caused by abutment is reduced and the sealing function can be performed more reliably.

Breast milk secreted from the nipple area N can pass through the cylindrical opening 41 from the internal space S2 and then can be guided to the exterior by the through-holes 31a, 31b and 31c of the outer member 30 which connect with the cylindrical opening 41, and then can be absorbed by the breast pad B.

Furthermore, the installation section 43 of the inner member 40 can have a wall portion which allows no gap and a bend section 44 which curves inwards formed integrally with the wall. Therefore, due to the bending and deforming function of the bend section 44, it is possible to make the deformable abutting section 45 deform appropriately and abut against the front face of the user's breast T.

Moreover, since the abutting and projecting section 46 can curve outwardly from the outer side of the deformable abutting section 45 and can cover the outer edge of the outer member 30, then it is possible to achieve suitable protection without the outer edge portion digging into the front face of the breast T or causing unpleasant irritation.

Furthermore, the uninterrupted wall portion which forms the installation section 43 can have a tapered shape which expands in diameter gradually toward the outer member 30, as indicated by reference numeral t1 in FIG. 3. Consequently, it is possible to prevent effectively local stagnation of breast milk which may collect in the internal space S2 that is demarcated by the wall portion, and the discharge of the collected breast milk to the exterior is facilitated.

Accordingly, the risk of breast milk leaking from the internal space S2 to the side of the breast T and soiling the user's clothing can be minimized. And, the milk can be absorbed appropriately by the breast pad B.

Furthermore, the injured nipple area N can remain dry, rather than being immersed in collected breast milk, and therefore the injury can heal more readily and growth of bacteria can be suppressed.

Furthermore, of the plurality of through-holes in the outer member 30, one of the through-holes 31a can be disposed below the virtual central line C1 in the vertical direction (height direction), as shown in FIG. 3 and FIG. 4. Therefore, all or most of the breast milk can be readily discharged to the exterior, rather than collecting in the lower portion of the internal space S2.

Moreover, in the inner member 40 large openings 42 can be formed in the left and right-hand outer sides of the cylindrical opening 41. Furthermore, since openings 32 having a larger surface area than the total opening surface area of the through-holes 31a, 31b, 31c can be provided in the outer member 30 at positions to the left and right-hand outer sides of the through-holes. Then, even though two or more members are used in the nipple protector 20, which combines an outer member 30 and the inner member 40, the weight can be reduced correspondingly by the large openings thus formed, and therefore the overall weight can be low. Consequently, the nipple protector 20 can be accurately positioned and the fitted state can be maintained satisfactorily.

Figure 6:
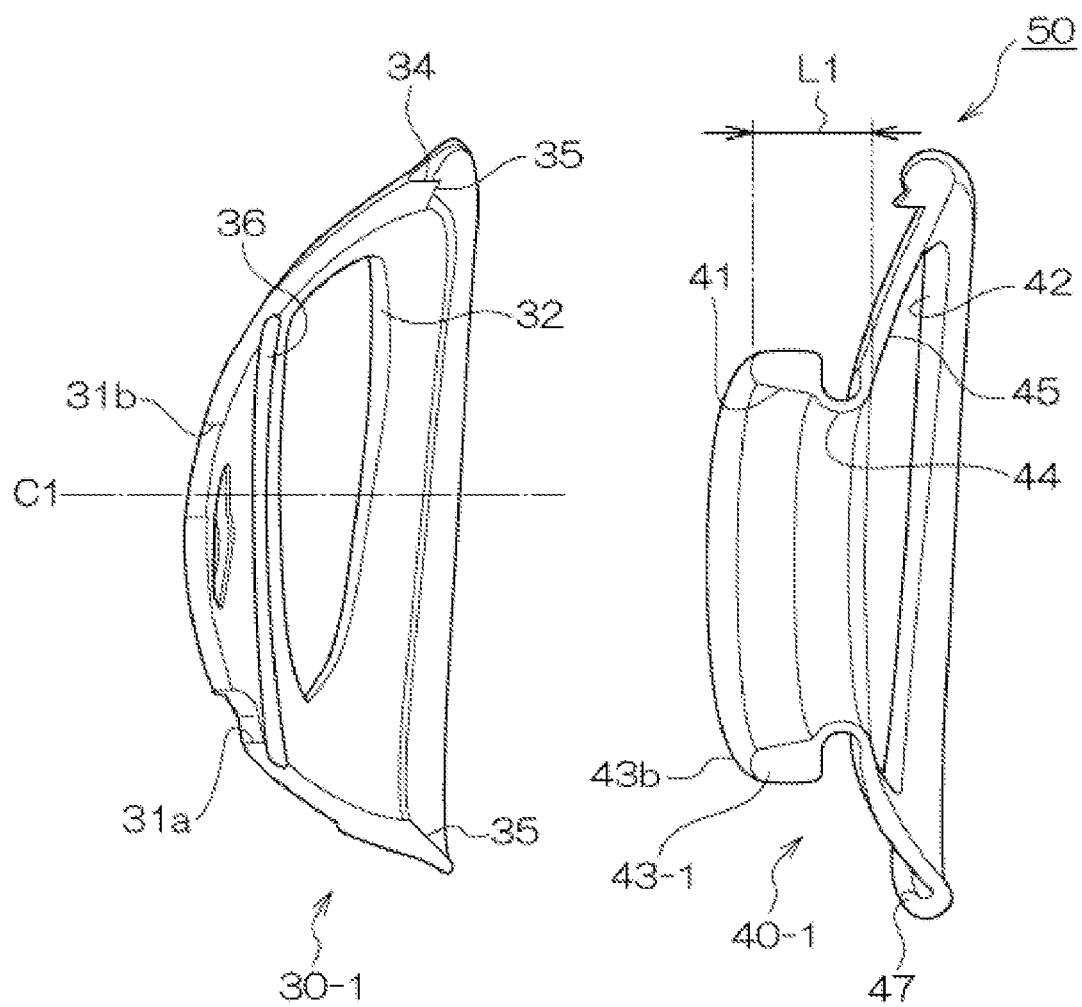
FIG. 6 is an exploded vertical cross-sectional view of a nipple protector according to a second embodiment of the disclosed subject matter.
Figure 7:
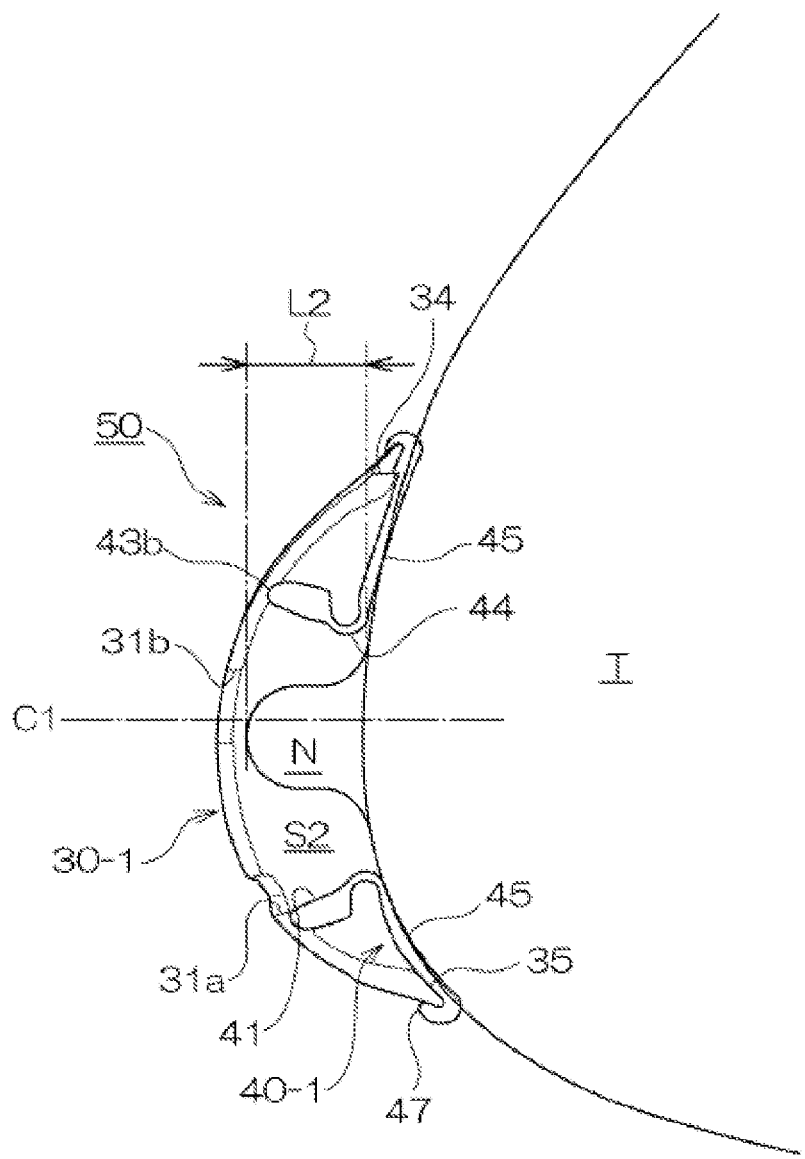
FIG. 7 is a vertical cross-sectional view showing a state where a user is wearing the nipple protector of FIG. 6.
Figure 8:
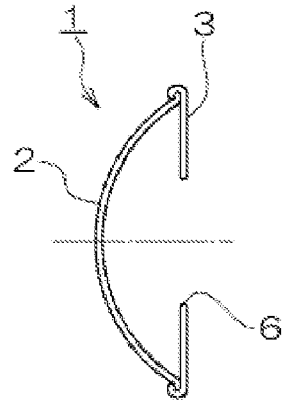
FIG. 8 is a cross-sectional view showing one example of a conventional nipple protector.
Figure 9:
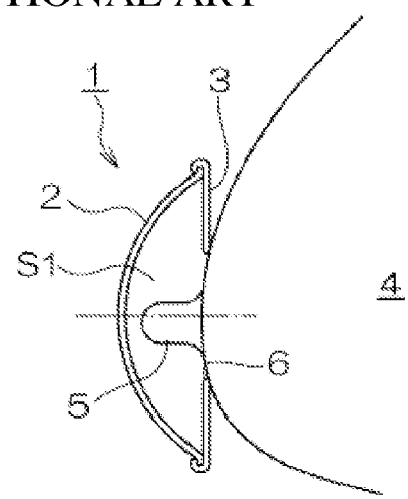
FIG. 9 is a cross-sectional view showing the nipple protector of FIG. 8 in a use state.
Figure 10:
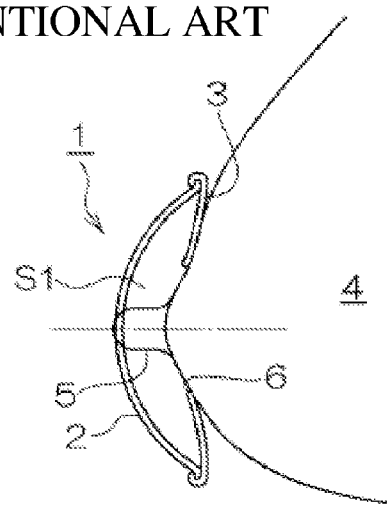
FIG. 10 is a cross-sectional view showing the nipple protector of FIG. 8 in a use state.

FIG. 6 and FIG. 7 show a second embodiment in accordance to the presently disclosed subject matter, FIG. 6 is an exploded side cross-sectional view, and FIG. 7 shows a fitted state (use state).

In these drawing figures, parts of the composition which are common or similar to the first embodiment are labeled with the same reference numerals and repeated description thereof is omitted. The following description centers on the points of difference.

In this embodiment, rather than forming the supporting section which is a cylindrical portion of the outer member 30-1, a cylindrical portion 43-1 can be formed only on the inner member 40-1. This cylindrical portion 43-1 can be a surrounding section which surrounds the perimeter of the nipple area of the user, and can have the form of a thick wall which can include a bend section 44 as well as having a sufficient height (length) L1. The bend section 44 can have a thickness that is less than the thickness of the cylindrical opening portion 41, such that the bend section 44 is relatively flexible as compared to the cylindrical opening portion 41.

As shown in FIG. 7, the cylindrical portion 43-1 can have at least the same height or a greater height than the average height (length) L2 of the nipple area of the user. The cylindrical portion 43-1 can abut against the inner surface of the outer member 30-1.

In a particular example, the dimension of L1 can be approximately 5 mm to 20 mm.

Furthermore, a groove section 36 forming an accommodating section as shown in FIG. 6 can be formed in the outer member 30-1. In other words, a portion for accommodating the front end portion 43b of the cylindrical portion 43-1, which forms a surrounding section extending from the inner member when the inner member 40-1 is assembled with the outer member 30-1 as shown in FIG. 7, can be formed on the inner side of the outer member 30-1 at the abutting position of the front end portion 43b. This accommodating section can be a groove section 36 which is a circular groove formed in a ring shape, for example.

According to the present embodiment, the cylindrical portion 43-1 extending from the inner member 40-1 can surround and protect the nipple area N of the user. Therefore, contact by the outer member 30-1 against the nipple area N can be avoided and this state of non-contact can be maintained (see FIG. 7).

Moreover, since the cylindrical portion 43-1 can be supported by the outer member 30-1, against which the cylindrical portion 43-1 abuts, then the volume of the internal space S2 formed by the cylindrical portion 43-1 can remain substantially unchanged during use and the nipple area of the user can be protected in an appropriate fashion. Furthermore, since the deformable abutting section 45 can be pressed appropriately against the front face of the user's breast T, then it is possible to achieve elastic contact in a reliable fashion.

Moreover, by providing a groove section 36, for example, to act as an accommodating section in the outer member 30-1, then the cylindrical portion 43-1 can be held accurately in a prescribed position on the inner surface of the outer member 30-1, and therefore the internal space S2 can be formed in an even more reliable fashion.

It should be noted that the present invention is not limited to the embodiments described above.

In the present embodiments, the cylindrical portion for forming the internal space can be formed respectively as a supporting section 33 of the outer member 30 and an installation section 43 of the inner member 40. But, it also can be formed only in either one of the outer member or the inner member.

Consequently, as also described in the second embodiment, the large opening which forms the internal space also can be formed in either one of the outer member 30 and the inner member 40. If the cylindrical portion is formed only in the outer member, then the front end portion of the cylindrical portion can be sufficiently covered by the inner member, so as to reduce to a minimum the irritation caused by abutment against the front face of the user's breast.

For the outer shape of the nipple protector 20, it is possible to employ various shapes other than a heart shape, such as a petal shape, a geometric shape, or the like. A design which has vertical orientation can be beneficial in making it possible to assemble and install the protector without errors, if, for example, the breast pad B has a similar vertical orientation.

Apart from being formed as two separate members as described above, the inner member and the outer member can also be formed as two-colored moldings or multi-colored moldings which combine the use of materials of different types, in a manner as described above.

Furthermore, the individual compositional elements of the embodiments described can be omitted, as desired, and combined with other compositions which are not described.

While there has been described what are at present considered to be exemplary embodiments of the invention, it will be understood that various modifications may be made thereto, and it is intended that the appended claims cover such modifications as fall within the true spirit and scope of the invention. All conventional art references described above are herein incorporated in their entirety by reference.

What is claimed is:

1. A method of using a nipple protector, comprising:
providing a rigid outer shell that defines an outer surface of the nipple protector and includes an inner surface spaced from and opposite to the outer surface, the outer shell made from a rigid material, and a flexible inner member made of a material more flexible than the rigid material of the outer shell, the inner member including a deformable abutting section connected to the rigid outer shell and configured to abut a user's breast, and a cylindrical section extending from the deformable abutting section toward the inner surface of the rigid outer shell;
attaching an outer peripheral area of the deformable abutting section of the inner member to the user's breast such that the inner member encircles the nipple of the user's breast and wherein the cylindrical section defines an opening having a central axis about which the inner member encircles the nipple of the user's breast;
attaching the cylindrical section to an inner portion of the outer shell at a location closer to the central axis than a location at which the outer peripheral area of the deformable abutting section is attached to the user's breast such that the inner member spaces the rigid outer shell from the nipple of the user's breast.

2. A nipple protector comprising:
an outer member having a hard shell shape which forms an outer surface of the nipple protector; and
an inner member made of a material which is more flexible and deformable than the outer member, with an internal space being formed inside the nipple protector, and
the inner member includes a deformable abutting section which deforms elastically and is capable of making close contact, with no gap, with a perimeter of a nipple area of a wearer,
wherein the internal space is formed by cylindrical portions which extend respectively from the outer member and the inner member, the cylindrical portion extending from the outer member forms a hard supporting section which surrounds the perimeter of the nipple area of the wearer, and the surrounding section which is the cylindrical portion extending from the inner member forms an installation section which covers the front end portion of the supporting section and also surrounds with no gap the nipple area completely.

3. The nipple protector according to claim 2, wherein the surrounding section of the inner member has a gapless wall section, and as a continuation from the wall section, a bend section which curves inwards on an inner side thereof is provided, and as continuations from the bend section, a deformable abutting section which expands outwards, and an abutting and protecting section which bends outwards on an outer side of the deformable abutting section and covers an outer edge of the outer member are provided.

4. The nipple protector according to claim 3, wherein the inner member includes an opening which connects the interior space surrounded by the surrounding section to the exterior, and the outer member includes a through-hole which connects to the opening.

5. The nipple protector according to claim 4, wherein a second opening defining a larger area than an area defined by at least one of the opening and the through-hole is formed in at least one of the inner member adjacent the opening and the outer member at a position adjacent the through-hole.

6. The nipple protector according to claim 2, wherein the inner member includes an opening which connects the interior space surrounded by the surrounding section to the exterior, and the outer member includes a through-hole which connects to the opening.

7. The nipple protector according to claim 6, wherein a second opening defining a larger area than an area defined by at least one of the opening and the through-hole is formed in at least one of the inner member at a position adjacent the opening and the outer member at a position adjacent the through-hole.

8. A nipple protector comprising:
an outer member having a hard shell shape which forms an outer surface of the nipple protector; and
an inner member made of a material which is more flexible and deformable than the outer member, with an internal space being formed inside the nipple protector, and
the inner member includes a deformable abutting section which deforms elastically and is capable of making close contact, with no gap, with a perimeter of a nipple area of a wearer,
wherein the internal space is formed by a cylindrical portion which is connected directly to and extends integrally from the inner member,
the cylindrical portion is a surrounding section which surrounds the nipple area when the nipple protector is located on a wearer, and a front end of the surrounding section abuts against an inner side of the outer member, and
the surrounding section of the inner member has a gapless wall section, and as a continuation from the wall section, a bend section which curves inwards on an inner side thereof is provided, and as continuations from the bend section, a deformable abutting section which expands outwards, and an abutting and protecting section which bends outwards on an outer side of the deformable abutting section and covers an outer edge of the outer member are provided.

9. The nipple protector according to claim 2, wherein the inner member includes an opening which connects the interior space surrounded by the surrounding section to the exterior, and the outer member includes a through-hole which connects to the opening.

10. The nipple protector according to claim 9, wherein a second opening defining a larger area than an area defined by at least one of the opening and the through-hole is formed in at least one of the inner member at a position adjacent the opening and the outer member at a position adjacent the through-hole.

11. A nipple protector comprising:
an outer member having a hard shell shape which forms an outer surface of the nipple protector; and
an inner member made of a material which is more flexible and deformable than the outer member, with an internal space being formed inside the nipple protector, and
the inner member includes a deformable abutting section which deforms elastically and is capable of making close contact, with no gap, with a perimeter of a nipple area of a wearer,
wherein the internal space is formed by a cylindrical portion which is connected directly to and extends integrally from the inner member,
the cylindrical portion is a surrounding section which surrounds the nipple area when the nipple protector is located on a wearer, and a front end of the surrounding section abuts against an inner side of the outer member, and
the inner member includes an opening which connects the internal space surrounded by the surrounding section to the exterior, and the outer member includes a through-hole which connects to the opening.

12. The nipple protector according to claim 11, wherein a second opening defining a larger area than an area defined by at least one of the opening and the through-hole is formed in at least one of the inner member at a position adjacent the opening and the outer member at a position adjacent the through-hole.

13. A nipple protector comprising:
a rigid outer shell that defines an outer surface of the nipple protector and includes an inner surface spaced from and opposite to the outer surface, the outer shell made from a rigid material; and
a flexible inner member made of a material more flexible than the rigid material of the outer shell, the inner member including,
a deformable abutting section connected to the rigid outer shell at a first position and configured to abut a user's breast, and
a cylindrical section extending from the deformable abutting section toward the inner surface of the rigid outer shell and connected to the rigid outer shell at a second position located inward of the first position,
wherein the cylindrical section defines an internal space configured to receive, without contact, a nipple area of the user's breast, and
the flexible inner member further includes a bend section connected to and located between each of the deformable abutting section and the cylindrical section, the bend section being made from a material that is relatively thinner than a material from which the cylindrical section is made.

14. The nipple protector according to claim 13, wherein the rigid outer shell further includes a supporting section extending from the inner surface of the rigid outer shell toward the flexible inner member and engages the cylindrical section of the inner member.

15. The protector according to claim 14, wherein:
the supporting section includes a cylindrical wall-shaped rib that includes an inside surface and an end surface; and
the cylindrical section includes a cylindrical opening extending therethough and an interlocking step section;
wherein the interlocking step section engages the inside surface and the end surface.

16. The nipple protector according to claim 13, wherein the inner surface of the rigid outer shell includes a groove section and the cylindrical section engages the groove section.

* * * * *

UNITED STATES PATENT AND TRADEMARK OFFICE
CERTIFICATE OF CORRECTION

| | | |
|---|---|---|
| PATENT NO. | : 8,056,563 B2 | |
| APPLICATION NO. | : 12/484432 | |
| DATED | : November 15, 2011 | |
| INVENTOR(S) | : Daisuke Yamashita | |

It is certified that error appears in the above-identified patent and that said Letters Patent is hereby corrected as shown below:

Col. 12, Line 60-64, claim 9 should read

9. The nipple protector according to claim 8, wherein the inner member includes an opening which connects the interior space surrounded by the surrounding section to the exterior, and the outer member includes a through-hole which connects to the opening.

Signed and Sealed this
Twenty-seventh Day of March, 2012

David J. Kappos
*Director of the United States Patent and Trademark Office*